US008786689B1

(12) United States Patent
Liu

(10) Patent No.: US 8,786,689 B1
(45) Date of Patent: Jul. 22, 2014

(54) MODULAR OPTICAL MEDICAL DIAGNOSTIC SYSTEM

(76) Inventor: Yongqian R. Liu, Richardson, TX (US)

( * ) Notice: Subject to any disclaimer, the term of this patent is extended or adjusted under 35 U.S.C. 154(b) by 765 days.

(21) Appl. No.: 13/085,482

(22) Filed: Apr. 13, 2011

Related U.S. Application Data

(60) Provisional application No. 61/324,638, filed on Apr. 15, 2010.

(51) Int. Cl.
*H04N 7/18* (2006.01)
(52) U.S. Cl.
USPC .......................................................... 348/68
(58) Field of Classification Search
USPC .......................................................... 348/68
See application file for complete search history.

(56) References Cited

U.S. PATENT DOCUMENTS

| 2008/0204589 A1* | 8/2008 | Chang | 348/373 |
| 2010/0190129 A1* | 7/2010 | Paz | 433/29 |
| 2010/0210951 A1* | 8/2010 | Rahman et al. | 600/476 |

* cited by examiner

*Primary Examiner* — Mehrdad Dastouri
*Assistant Examiner* — Mohammed Rahaman

(57) ABSTRACT

An optical medical diagnostic system is disclosed comprising a LED light assembly, a controller portion and a power portion where the modular LED light assembly can switch from one operating wavelength LED light assembly to another wavelength LED light assembly. The generated fluorescence image may be viewed through a fluorescence band pass filter assembly mounted on the light handle and viewing angle can be adjusted through its tilt arm. The band pass filter blocks the excitation wavelength and passes the fluorescence wavelength.

17 Claims, 15 Drawing Sheets

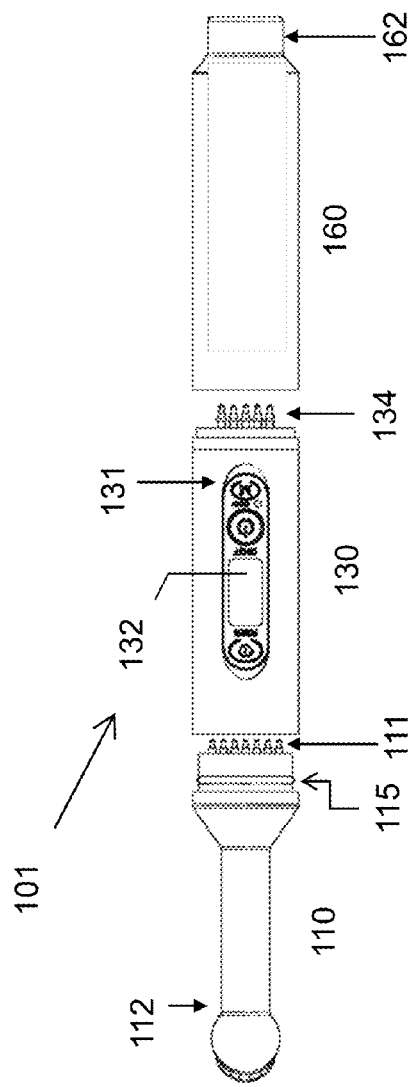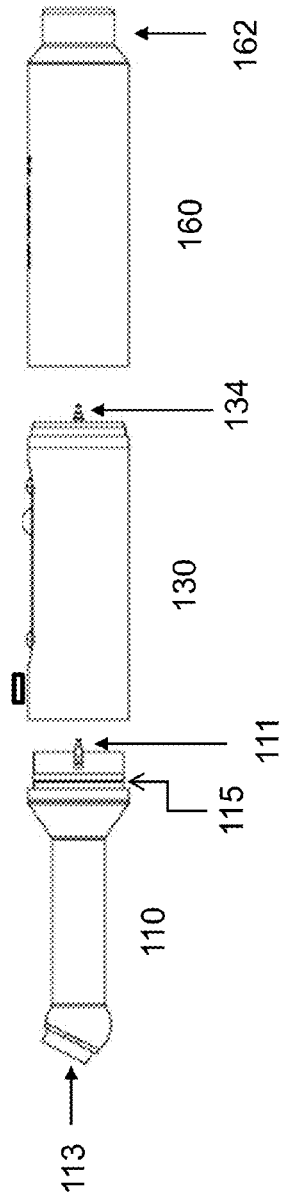
FIG. 1A
FIG. 1B

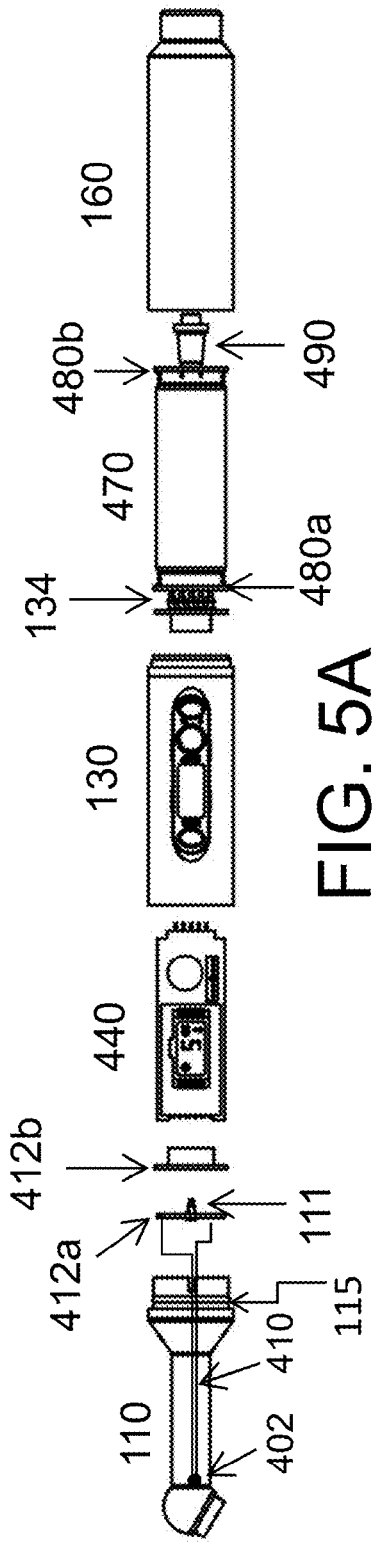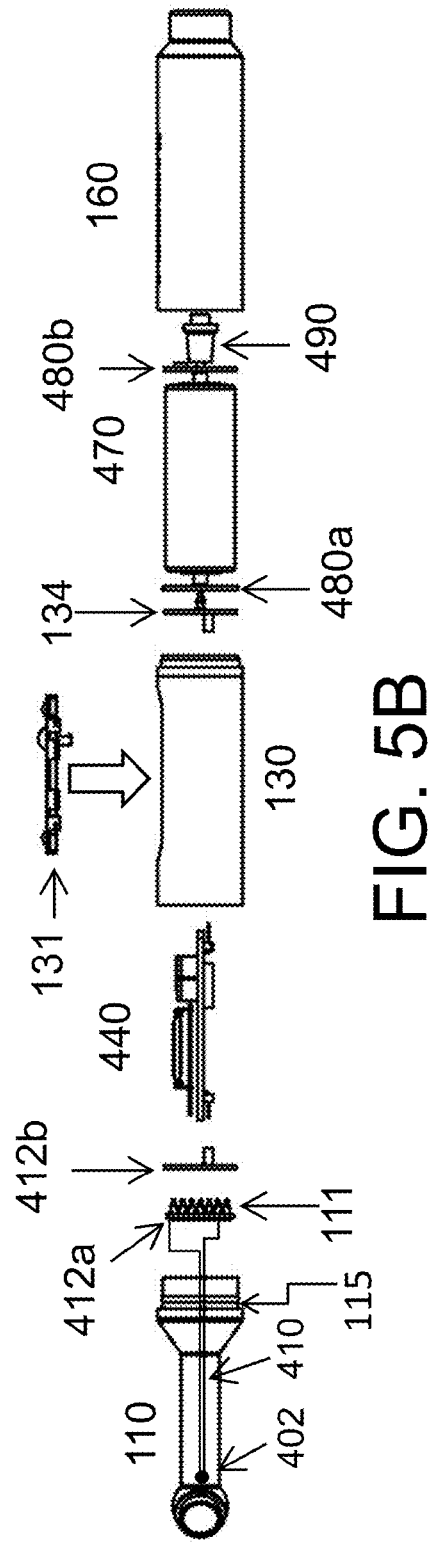

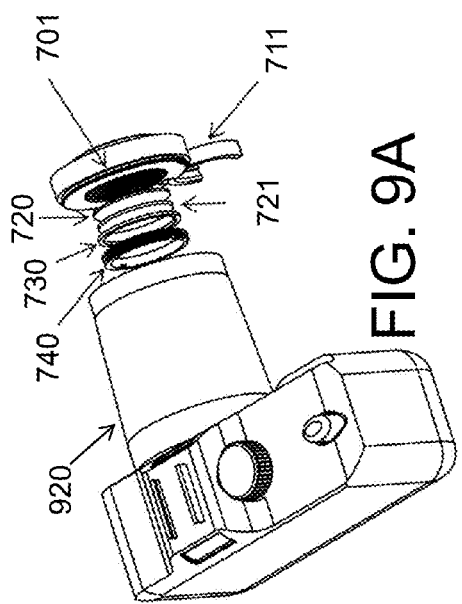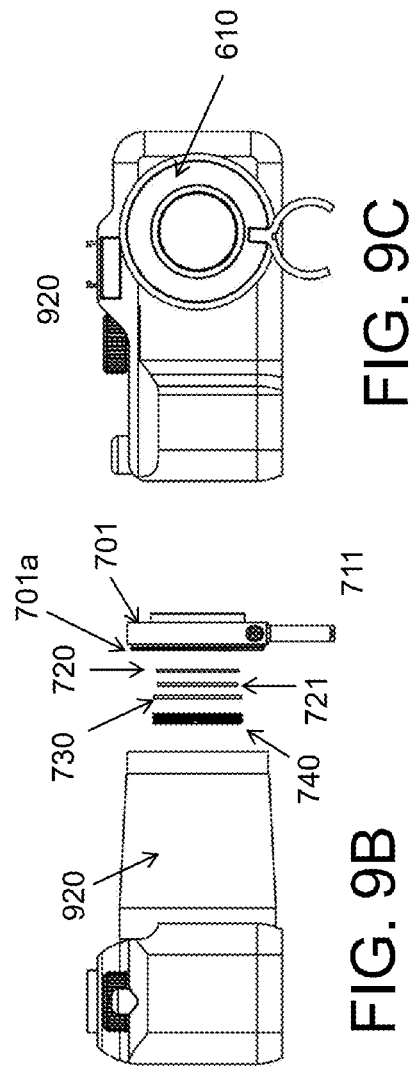

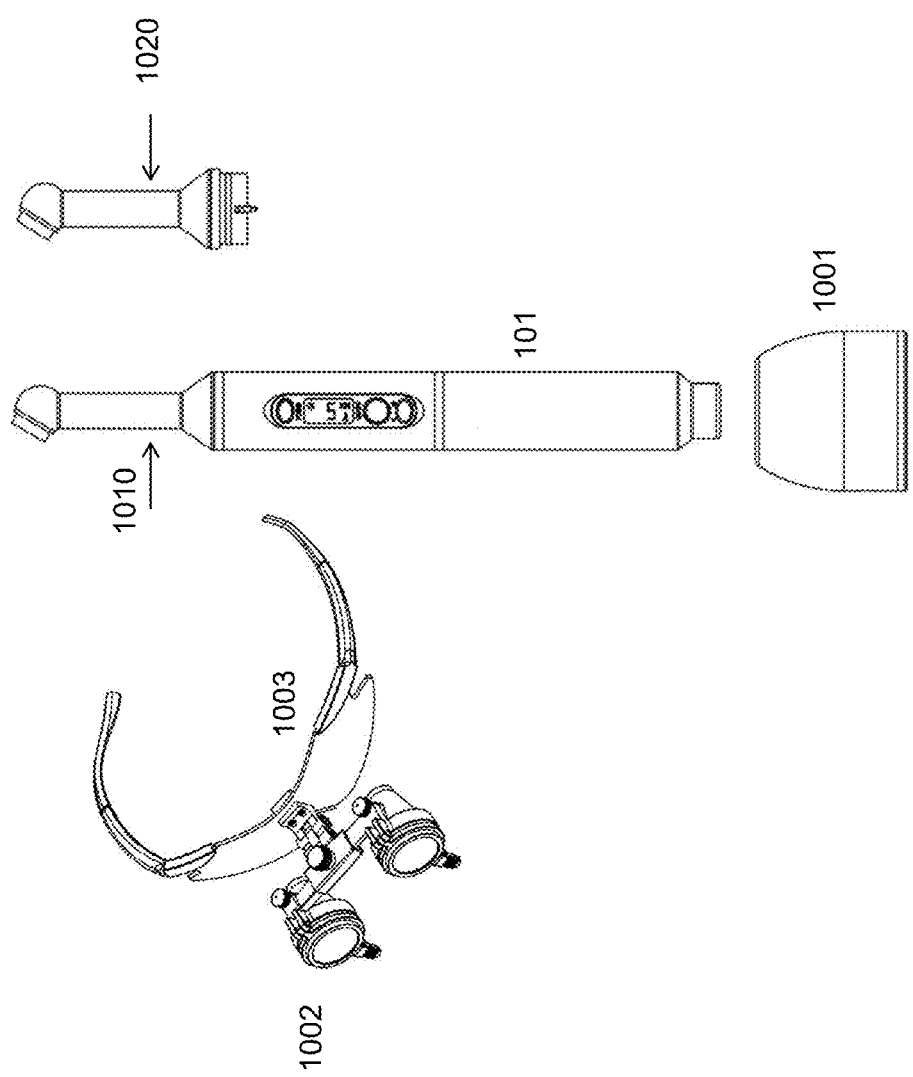

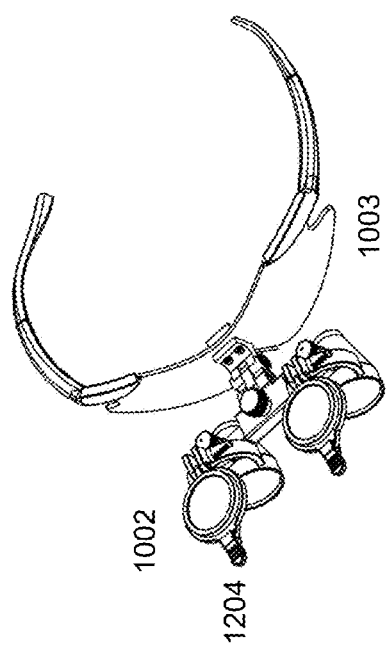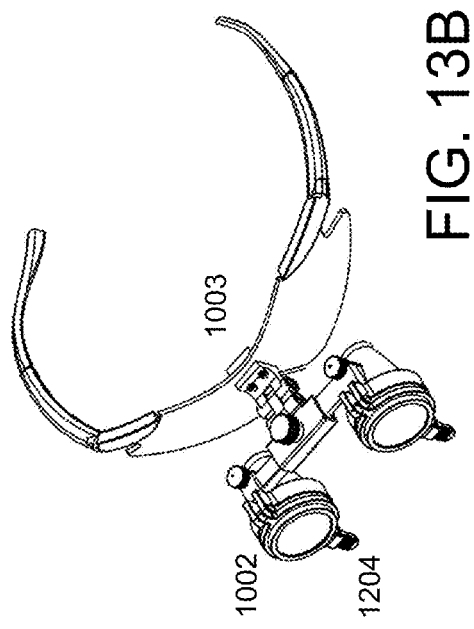

US 8,786,689 B1

MODULAR OPTICAL MEDICAL DIAGNOSTIC SYSTEM

CROSS REFERENCE TO RELATED APPLICATIONS

This application claims the benefit of the filing date of U.S. provisional patent application Ser. No. 61/324,638, entitled Modular Oral Exam Light, filed on Apr. 15, 2010, the disclosure of which is incorporated herein by reference for all purposes. This application claims also incorporates by reference for all purposes U.S. Pat. No. 7,857,619, entitled LED Curing Light Having Fresnel Lenses, issued to the Applicant on Dec. 28, 2010.

TECHNICAL FIELD

The invention relates generally to the field of oral cavity illumination, and in particular to tissue and cavity diseases detection through fluorescence.

BACKGROUND INFORMATION

Oral cancer affects over 30,000 people today in US alone. The treatment of this disease is most effective when detected early. One useful technique in detecting early oral cancer is through the distinction of tissue fluorescence from healthy and abnormal tissue.

The basic physics of the fluorescence and reflectance imaging have been known to produce fluorescence contrast image maps, which assists identification of early malignant tissue.

However, implementation of the fluorescence contrast techniques for practical applications in a practitioner's office have been limited due to various reasons, including the performance and cost of implementation. A need exists, therefore, for an optical medical diagnostic apparatus or system that can be used easily and efficiently in a practitioner's office.

SUMMARY

In response to these and other problems, there is disclosed various embodiments of a system for a practical optical medical diagnostic system.

In one embodiment, there is disclosed an optical device including a modular LED optical medical diagnostic system comprising an LED light assembly, controller portion and power portion where the modular LED light assembly can switch from one operating wavelength LED light assembly to another wavelength LED light assembly. In one embodiment, the generated fluorescence image may be viewed through a fluorescence band pass filter assembly mounted on the light handle and viewing angle can be adjusted through its tilt arm. The band pass filter that may block much of the excitation wavelength and may pass most of the fluorescence wavelength.

In one embodiment, the generated fluorescence image may be viewed through a switchable magnification loupe adapting band pass filter system that may block much of the excitation wavelength and may pass most of the fluorescence wavelength.

It is to be understood that both the foregoing general descriptions and the following detailed description are merely exemplary of the invention, and are intended to provide an overview or framework for understanding the nature and character of the invention as it is claimed. Additional features and advantages of the invention will become apparent from the following drawings and description. The drawings illustrate various embodiments of the invention and together with the description serve to explain the principles and operations of the invention.

BRIEF DESCRIPTION OF THE DRAWINGS

The above and further advantages of this invention may be better understood by referring to the following description taken in conjunction with the accompanying drawings in which like numerals designate corresponding elements or sections throughout, and in which:

FIG. 1A is an exploded top view of the light portion of an optical medical diagnostic system.

FIG. 1B is an exploded side view of the light portion of an optical medical diagnostic system.

FIG. 5A is an exploded top view of the light portion of an optical medical diagnostic system.

FIG. 5B is an exploded side view of the light portion of an optical medical diagnostic system.

FIG. 9 shows an assembly view of optical filters with recording camera.

FIG. 10 shows another embodiment of an optical medical diagnostic system.

FIG. 13A is an isometric view illustrating a fluorescence loupe filter coupled to the magnification loupes of an eye glass assembly in a first configuration.

FIG. 13B is an isometric view illustrating a fluorescence loupe filter coupled to the magnification loupes of an eye glass assembly in a second configuration.

DETAILED DESCRIPTION

Figure 2:
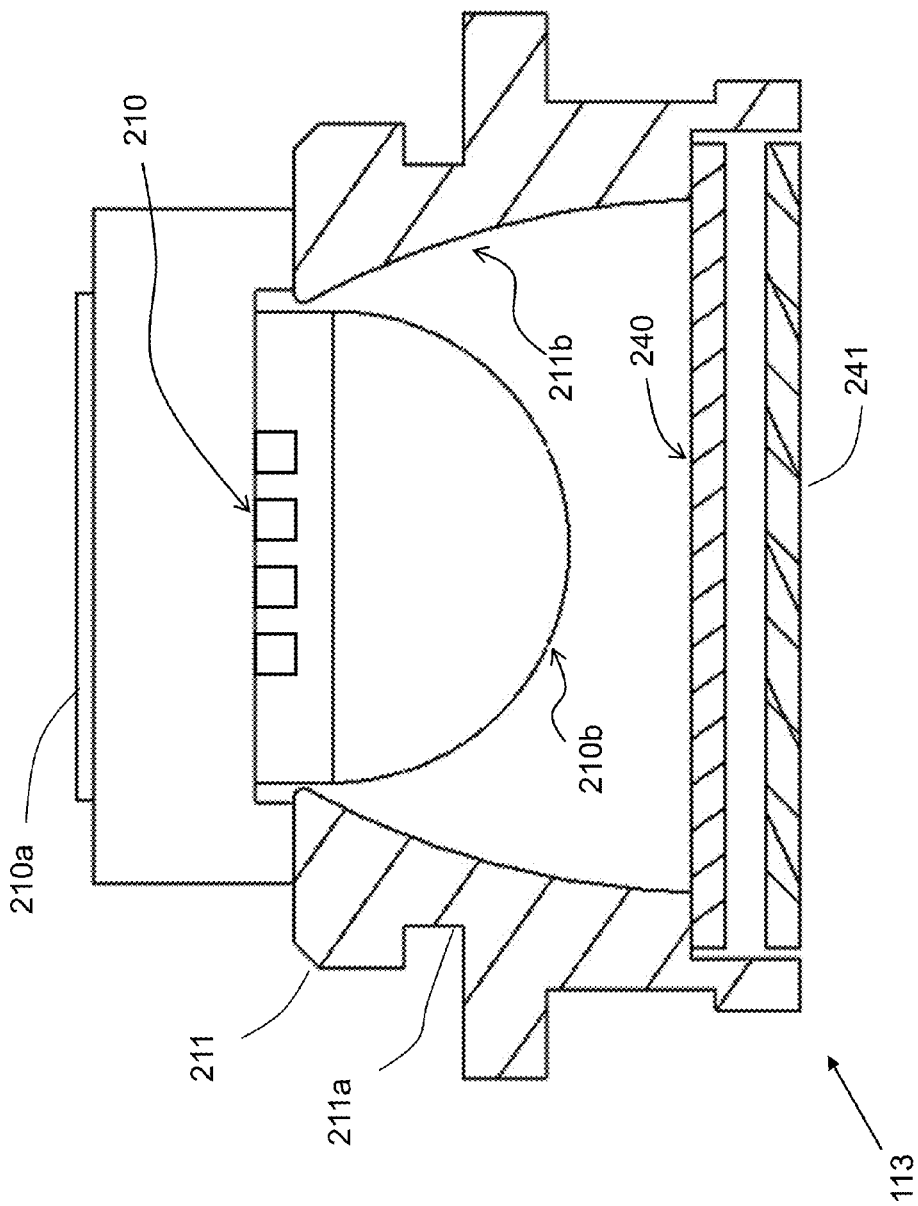
FIG. 2 is a sectional view illustrating one embodiment of an optical lens module.

For the purposes of promoting an understanding of the principles of the present inventions, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the inventions as described herein are contemplated as would normally occur to one skilled in the art to which the invention relates.

FIG. 1A is a top view and FIG. 1B is a side view of one embodiment of an optical illumination system or light portion 101 for modular LED optical medical diagnostic system. The light portion 101 comprises a LED light assembly 110, a controller portion 130, and a power portion 160.

The LED light assembly 110 is modular or detachable from the controller portion 130. The LED light assembly 110 includes a plurality of spring-loaded contact pins 111 on a driving circuit board (not shown) for the LED, LED housing chamber 112 and light management optical lens assembly 113. The LED light assembly 110 mechanically connects to the controller portion through tight fit and holding fixture mechanism. An example holding fixture mechanism includes an O-ring 115 positioned near the distal end of the light assembly 110 that fits tight into a ring slot inside the near end of the controller portion 130. The modular mechanical connection between the light assembly 110 and the controller portion 130 allows the light assembly 110 to be able to rotate circularly 360 degrees around the controller portion with the longitudinal housing as the axis of rotation for easier access to different angles and locations inside the target illumination area.

Additionally, the modular connection mechanism allows interchanging the light assembly 110 from one operating wavelength light assembly, for example, a standard 380-430 nm high power violet light assembly with another wavelength light assembly, for example, standard high power white light assembly (5000-7000 K color temperature).

Illuminating target tissue with different wavelength light assembly allows inspection of tissue through fluorescence, absorption or reflectance spectrum to make more accurate determination of the health condition of tissue. The modularity allows users to select the correct light assembly for examination.

The electrical connection of light assembly with the controller portion is achieved through the spring-loaded contact pins 111, which receive driving current from and send thermal alarm signal to the control circuitry inside the controller portion 130.

The high power LED is mounted in the proximal end of light assembly or housing chamber 112 and its optical beam managed and directed by the optical lens assembly 113. The LED light assembly 110 is preferably made of high thermal conducting materials including aluminum and copper to transfer and dissipate heat efficiently.

The controller portion 130 includes a control interface 131, a control function display 132 and spring-loaded electrical contact pins 134. The control interface 131 includes control keys or buttons preferably made of metal keypads. The control function display 132 displays the operating time and operating state of the light such as timing set, timer count, and operating mode including constant power and pulsed. The spring-loaded electrical contact pins 134 includes spring-loaded metal pins mounted circuit board that connect controller portion with the power portion to supply voltage, current and charging electricity.

The power portion 160 is modularly constructed to connect with the controller portion. A neck shaped tail end 162 enables the light unit to be mounted on a table top and dental unit bar mechanical holder for electrical charging or directly plugged into an AC/DC power adapter for battery charging.

FIG. 2 illustrates an LED and optical lens assembly 113 including a high power LED 210 with multiple diode chips packaged in a single diode, directional collimating hyper-hemispherical lens 210b, diode heat sink 210a, a Fresnel collimating lens 240, a transparent lens protecting disk 241, and a lens mounting assembly 211. The light emitted from LED 210 typically has a divergence angle of over 80 degrees after passing through co-packaged lens 210b.

The lens mounting assembly 211 includes a mounting thread 211a and a high reflectance parabolic surface 211b. The mounting threads 211a mounts the LED illumination optical lens assembly 113 to the LED housing chamber 112 as will be discussed in detail below. The high reflectance parabolic surface 211b redirects the high divergence angle beam to a narrower diverging beam. The high reflectance parabolic surface 211b provides reflectivity of over 95%, for example 98%, at the LED emitted wavelength range. Example materials the lens mounting assembly 211 are copper and aluminum. Electroplating of the high reflectance parabolic surface 211b with chromium, zinc, aluminum, and silver offers the desired high reflectivity. Alternatively, high reflective thin films such as multiplayer metal oxide or polymer films can be evaporated or coated and post mounted at the high reflectance parabolic surface 211b to achieve the desired results.

The proposed LED collimating lens is a thin disk of Fresnel collimating lens 240 with a focus length of 2 to 10 millimeter. The embodiment of the current invention enables collimation of LED illumination with minimum coupling loss, a desired spot size limited by diffraction from source chip size and a minimum thickness in the lens assembly. The Fresnel lens includes circular grooves that refract light with different angles at different radial position to form the function of a lens. They can be formed by either constant grooves spacing or constant groove height. Constant groove height is preferred for the Fresnel lens in oral exam applications.

The Fresnel collimating lens 240 and the transparent lens protecting disk 241 can be made of transparent materials such as polycarbonate, acrylic, silicone, rigid vinyl and others that are low cost through compression or injection molding or laser engraving of large piece of materials enabling wafer level productions that make them low cost. The Fresnel lens 240 and the transparent lens protecting disk 241 can be assembled together through standard packaging procedures such as bonding or sealing them to the interior rim on the proximal end of the lens mounting assembly 211.

Alternative injection molded acrylic or polycarbonate spherical or aspherical lens can be also used to achieve a well collimated beam.

Figure 3:
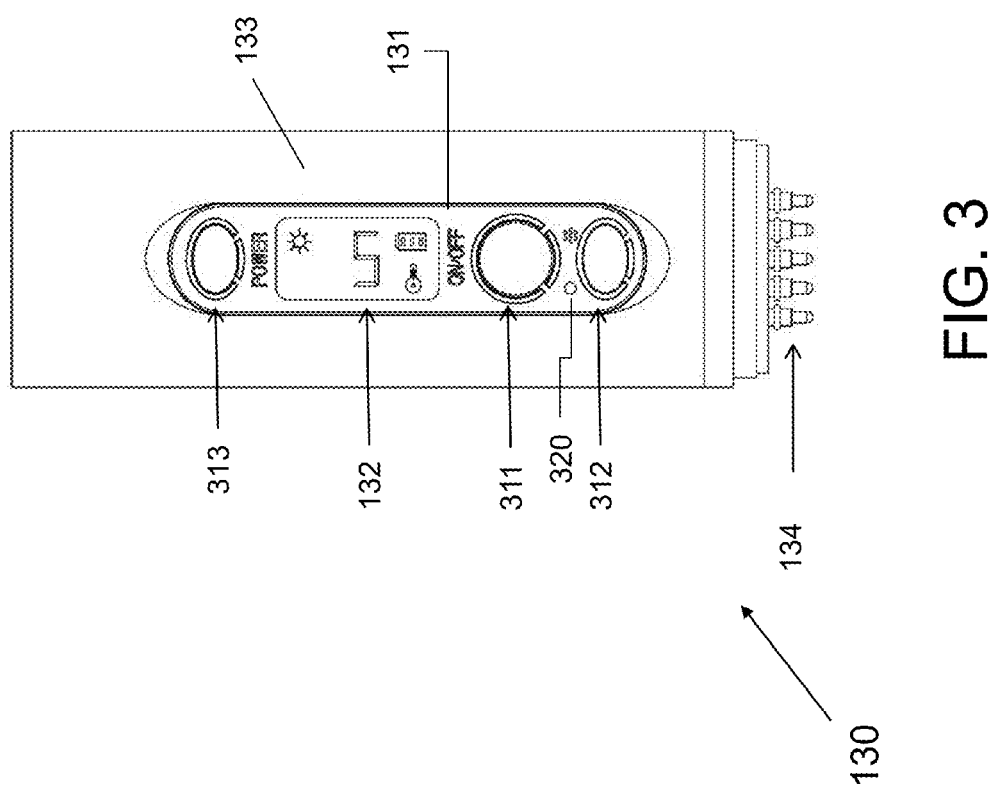
FIG. 3 shows an embodiment of the controller unit of the light portion of an optical medical diagnostic system.

FIG. 3 illustrates in detail one embodiment of the controller portion 130 including a controller housing 133 with control interface 131 and LCD control function display 132. In certain embodiments, the control interface 131 includes three control keys or buttons: a unit power key 313, a light on/off key 311, and a operation mode menu key 312. Unit power key 313 enables/disables the unit display and sets operating power. Light on/off key 311 activates and deactivates the light portion 101. Mode menu key 312 selects pre-programmed timing sequence and operating mode of the light for safety protection. LED indicator 320 indicates the charging state and alarm state of the light. The electrical interface 134 enable modular electrical connections from power portion to the controller portion through spring-loaded electrical connection pins.

Figure 4:
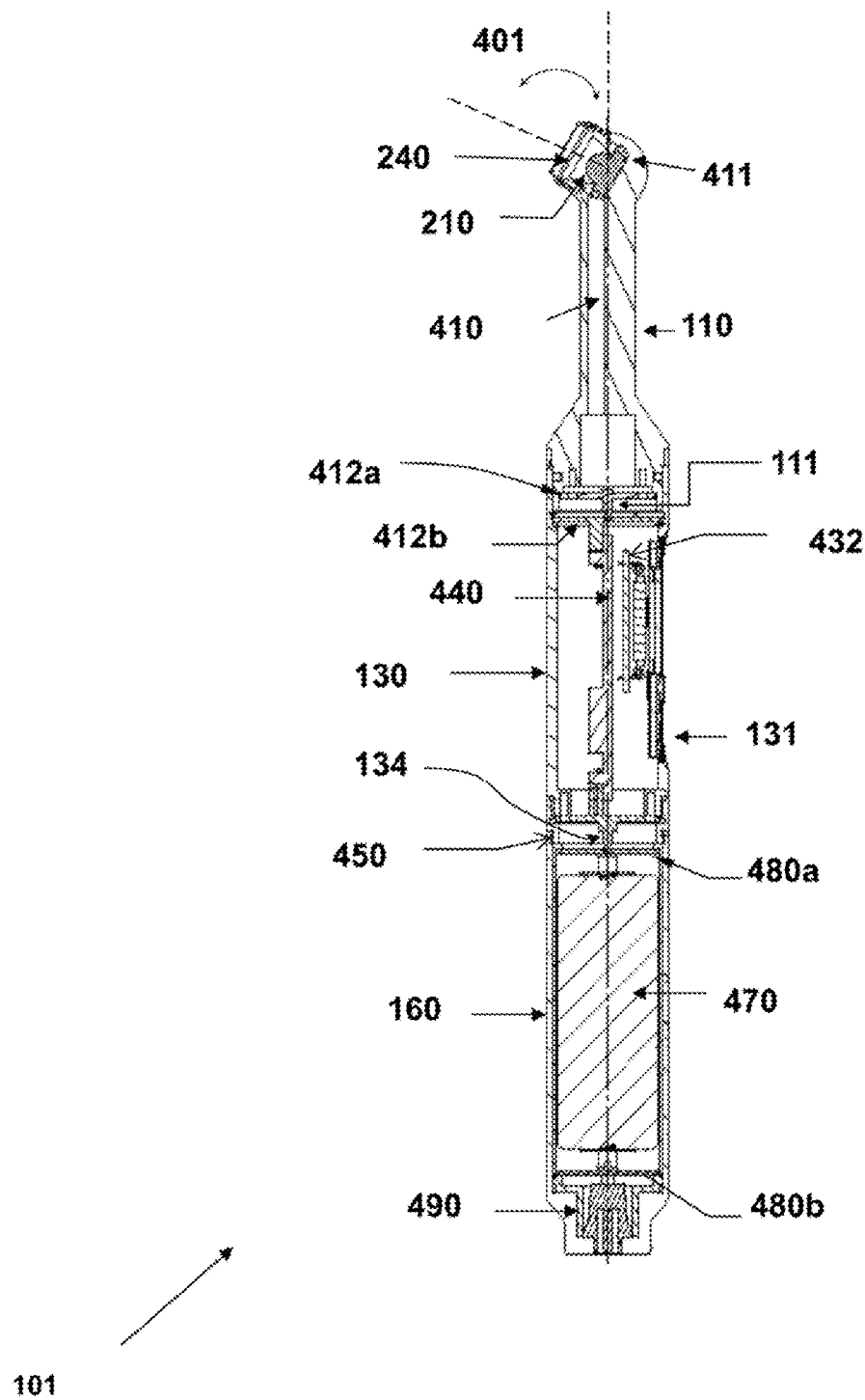
FIG. 4 is a cross sectional view of the light portion of an optical medical diagnostic system.

FIG. 4 illustrates a cross section view of the light portion 101, which includes the modular LED light assembly 110, the modular controller portion 130, and the modular power portion 160. The light portion has a longitudinal housing portion is preferably made of highly heat conductive materials such as aluminum and copper to enhance heat dissipation speed.

The LED light assembly is positioned at a distal end of the longitudinal housing with light beam directing at a predetermined angle 401 between 5 and 90 degrees and preferably around 25 degrees for ease of access to deep throat with sufficient line of sight clearance for fluorescence filter.

As discussed in reference to FIG. 2, the LED light assembly 110 includes a high power LED 210 and Fresnel collimating lens 240 for light beam management. The light assembly 110 provides heat dissipation for the LED generated heat through mounting interface 411 bonded by thermal epoxy between the backside of the LED 210a and the mounting surface 411. The light assembly 110 is mechanically coupled to a proximal end portion of the longitudinal housing of controller portion through mechanical tight fit and spring-loaded contact pins 111.

The LED 210 is powered by a control circuit board 440 through control connection board 412b via spring-loaded contact pins 111 mounted on the LED drive board 412a. The control circuit board or controller circuitry 440 resides in the controller housing 130 and interfaces with control interface 131 through daughter circuit board 432. The control circuitry 440 is activated by a light on/off key 311 and powered by a high energy density rechargeable battery 470 within the power portion 160. The control circuitry 440 performs DC-DC conversion to the desired constant driving current sent to the LED 210. The control circuitry 440 also presets exposure timing sequence, alarms low battery indicator LED 320 and sends warning signal to LCD display for automatic shut off. Additionally, the control circuitry 440 receives thermal control signals through a thermal sensor 402 mounted in the light assembly placed in close proximity to the LED via two conducting lead wires 410 and shuts down LED when LED temperatures exceed safety settings. The LCD display preferably displays the state of the battery 470, thermal alarm indication, operating mode (constant or pulsed), and time settings.

A high energy density rechargeable battery 470 is housed in the power portion 160. The power portion is modular or detachable from the controller portion. The battery 470 is electrically connected with two circular circuit boards 480a and 480b and is tight fit into the power portion 160 longitudinal housing. The circuit board 480a electrically connected with the control circuit board 440 via spring-loaded electrical contact pins 134 and metal rings on circuit board 480a to supply voltage and current to the controller portion. The power portion 160 is connected with the distal end of the controller portion 130 housing through a mating thread 450. The circuit board 480b interfaces with an external power adapter through a small molded pin connector 490. The combined circuit board of 440, 134, 480a, and 480b also performs the smart charging circuit to safely charge the rechargeable battery 470.

The rechargeable battery 470 is preferably a lithium ion battery that has nominal voltage of 3.7-4.2V. A single battery with sufficient energy capacity is typically sufficient for oral exam light operation although multiple batteries can extend the standalone operation time.

FIG. 5A is a top exploded view of one embodiment of the light unit 101. FIG. 5B is a side exploded view of one embodiment of the light unit 101. Referring to both FIGS. 5A and 5B, there is the light assembly 110, controller portion 130 and power portion 160.

Electrical connection is made between the light assembly and controller portion through spring-loaded contact pins 111 on circuit board 412a and connection board 412b plugged in controller circuitry board 440. Mechanical connection is made between the light assembly and controller portion through retaining O-rings 115 and tight fit between the proximal end portions of the longitudinal housing. Over temperature is monitored by thermistor 402 through two lead wires 410 connected to the circuit board 412a and communicated with the controller circuitry board 440.

The controller portion has control circuitry board 440 powered by the power portion through electrical interface spring loaded connection pins 134 whose mounting circuit board is plugged into the control circuitry board 440. The control circuitry board 440 is further set and activated by the control interface 131 and send driving current to light assembly.

The power portion 160 includes a rechargeable battery 470, circuit boards 480a and 480b, and molded charge pin connector 490.

Figure 6:
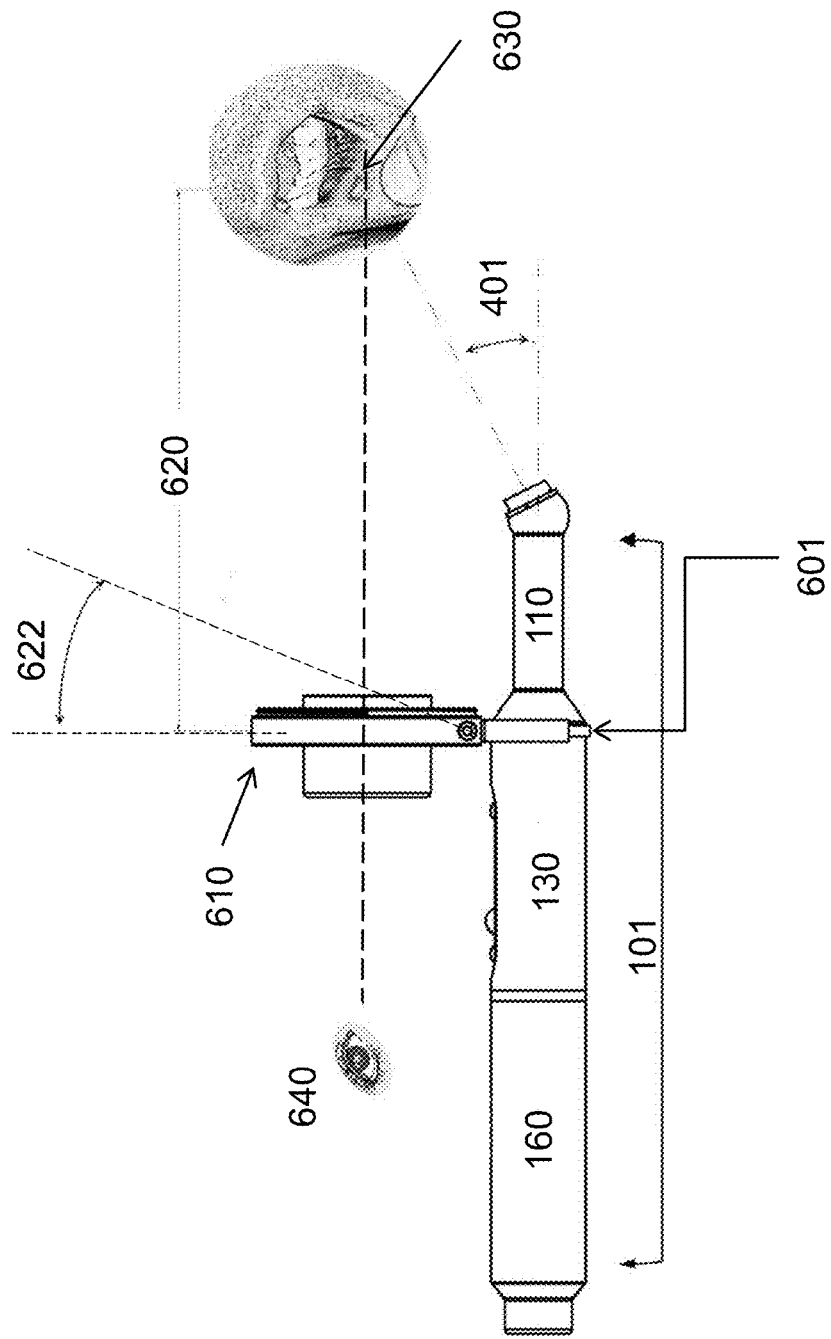
FIG. 6 shows one embodiment of an optical medical diagnostic system.

FIG. 6 illustrates one embodiment of a cordless optical medical diagnostic system and its use. It shows a two dimensional side view of the light portion 501 and a fluorescence filter assembly 610.

The light portion 101 includes a LED light assembly 110, controller portion 130, and power portion 160 where the light assembly 110 directs the illumination light at an angle 401 of around 25 degrees toward examination target 630.

In certain embodiments, the filter assembly 610 clip-on connects to the distal end of the light portion 101 with a mounting ring 601. The filter assembly 610 blocks the illumination light from the examination target and enables viewing the fluorescence from the examination target 630 at a distance 620 typically in the range of 1 to 7 inches (which is sufficient for back throat examination with a clinician's eye 640). The filter assembly 610 can be adjusted in its tilt angle 622 relative to the longitudinal housing of the light portion 101 for easy direct viewing of the examination targets such as oral cavity at variable distances from the light portion 101.

Figure 7:
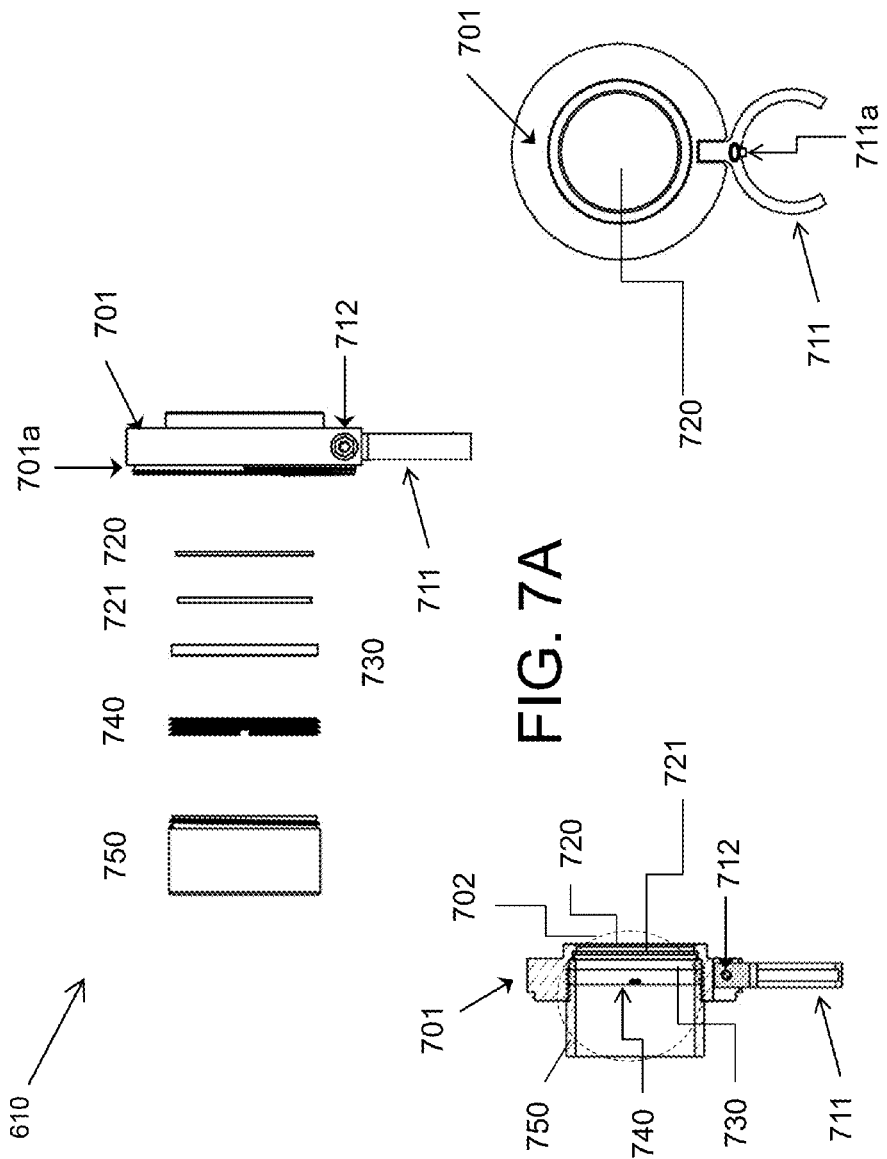
FIG. 7A is a exploded side view of one embodiment of an optical filter assembly.
FIG. 7B is a section view of the embodiment of an optical filter assembly of FIG. 7A.
FIG. 7C is a front view of one embodiment of an optical filter assembly of FIG. 7A.

FIG. 7A is an exploded side view of one embodiment of a filter assembly 610. FIG. 7B is a section view of the filter assembly 610. FIG. 7C is a front view of the filter assembly 610. Referring to FIGS. 7A, 7B, and 7C, one can see that the filter assembly 610 comprises a filter holder 701 connected with a semi-circular mounting clip 711 through a mounting screw 712. The filter holder 701 has a filter cavity 702 sized to receive and retain at least a first fluorescence filter 720, and preferably a second fluorescence filter 721, a shock absorbing rubber ring 730, a retaining ring 740 to hold the filters in place inside the filter cavity 702. The retaining ring 740 has exterior mounting threads adapted to couple the retaining mounting threads from the internal surface of the filter cavity 702. To prevent ambient light reflection and infection control protection, a light hood 750 having exterior mounting threads is further adapted to couple to the filter cavity 702 mounting threads.

The semi-circular mounting clip 711 is preferably made of flexible plastics including polyoxymethylene and has a center notch 711a for easy and secure connection with the light assembly 110 on its mounting ring 601. In certain embodiments, the semi-circular mounting clip 711 can also easily snap off and detach from the light assembly 110 as a result of its flexible semi-circular structure. On the distal side of the filter holder 701 is a mounting thread 701a for mounting the filter assembly 610 on a digital camera for case documentation after it detaches from the light assembly 110 as explained further below.

Figure 8:
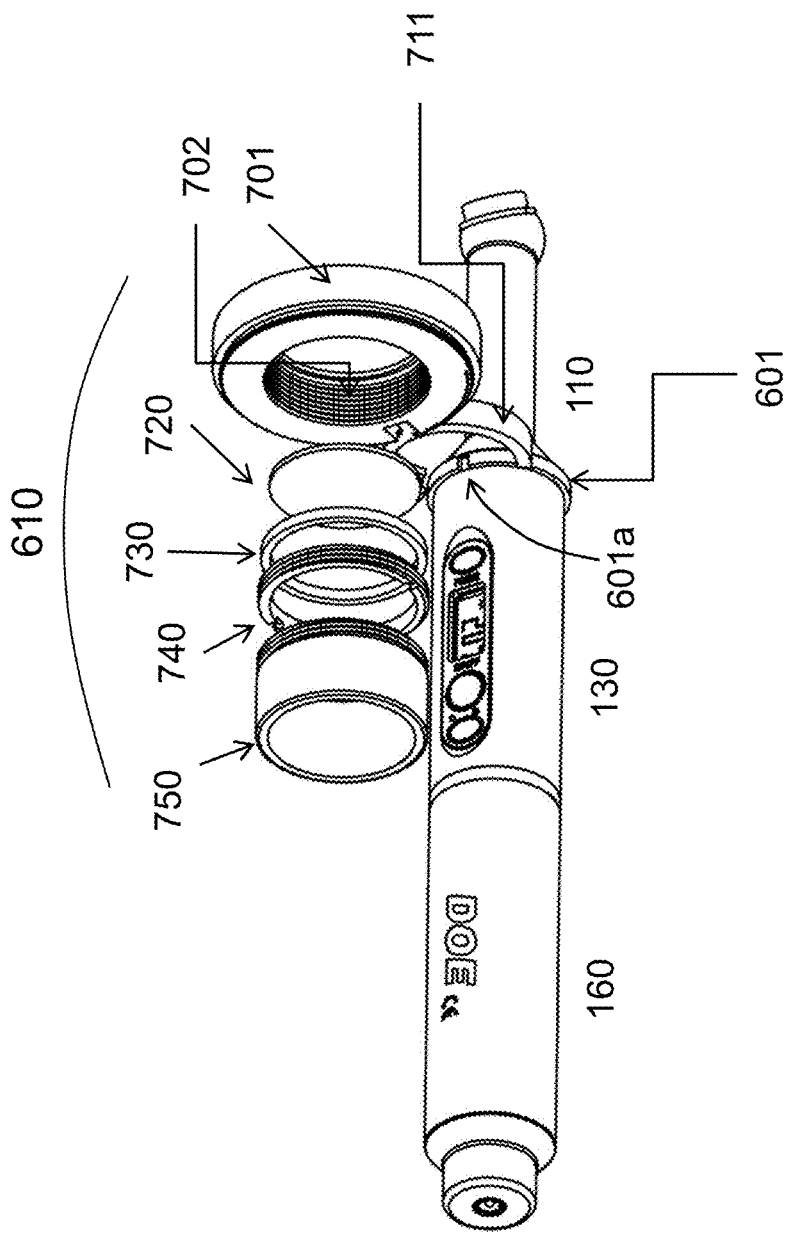
FIG. 8 shows an isometric assembly view of an optical medical diagnostic system.

FIG. 8 is a 3-dimensional assembly schematic of the preferred embodiment of the optical medical diagnostic system including the light portion 101 and filter assembly 610. The filter assembly 610 includes the semi-circular mounting clip 711 connected to the filter holder 701 that has a filter cavity 702 to receive the fluorescence filter 720, the shock absorbing rubber ring 730, the retainer ring 740 that has exterior mounting threads and the light hood 750 having the same exterior mounting threads that are adapted to couple to the retaining mounting threads from the internal surface of the filter cavity 702.

The semi-circular mounting clip 711 snaps and mates with a mounting groove 601a on the mounting ring 601 at the distal end of the light assembly 110 through its center notch 711a and flexible tight fit. This prevents the filter assembly 610 from both rotating out of view or accidental falls. The combined assembly of the filter assembly 610 and the light assembly 110 allows them to rotate 360 degrees together relative to the controller portion 130 and power portion 160 the long axis of the longitudinal housing. This significantly eases the access of the light and viewing angle to anywhere inside the oral cavity.

The light hood 750 prevents ambient light reflection from the filter surface into viewing eye. This eases the diagnostic and exam procedure without the need of turning off ambient light.

FIG. 9 illustrates the use of the filter assembly 610 for case documentation with a digital camera 920. Once the filter assembly 610 snaps off and detaches from the light assembly 110, it can be thread mounted onto standard digital camera lens through the exterior mounting thread 701a with a diameter between 20 and 60 millimeters and preferably 58 millimeters. For cameras with other sizes, a step down or step up ring may be used to adapt the same filter assembly to a particular camera lens size. To document a case, a user may simply shine the illumination light from the light portion 101 on the target area and take motion or still fluorescence images from the digital camera 920 coupled to the filter assembly 610.

FIG. 10 illustrates another embodiment of an optical medical diagnostic system including light portion 101, a charging stand 1001, two fluorescence loupe filter assembly 1002, flip-up magnification loupes 1003, and additional light assembly 1020. The default light portion 101 includes the light assembly 1010 with excitation light wavelength preferably in the violet wavelength of 380-430 nm. The additional light assembly 1020 includes light wavelength preferably in the white light wavelength (5000-7000 K color temperature).

The white light assembly 1020 provides oral illumination for enhanced viewing and secondary transillumination of teeth for cracks and early caries detection. The Violet light assembly 1010 provides fluorescence excitation.

Optionally, the kit may include an inter-changeable light assembly of other colors. Green (500-580 nm) wavelength source light assembly provides enhanced reflectance viewing. Blue (430-490 nm) wavelength source light assembly provides either alternative fluorescence excitation wavelength and/or a compelling fast composite curing light as an additionally function of the optical medical diagnostic system as detailed in U.S. Pat. No. 7,857,619, entitled LED curing light having Fresnel lenses, issued to the Applicant on Dec. 28, 2010.

Figure 11:
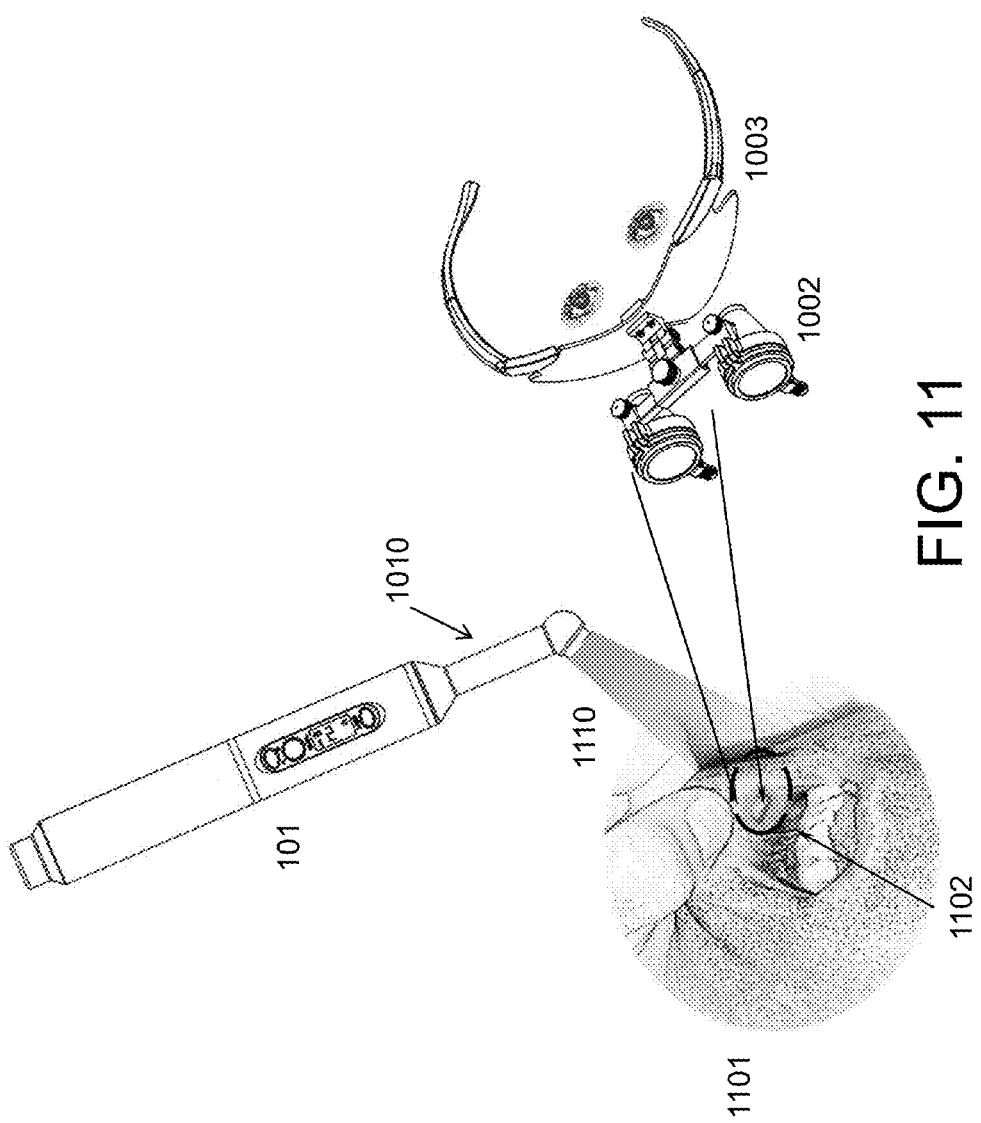
FIG. 11 shows an operation schematic of the optical medical diagnostic system of the second embodiment.

FIG. 11 illustrates the operation schematic. To operate, it is recommended that the patient puts on protective eyewear goggle. The white light assembly 1020 may then be mounted in the light portion 101. The unit may be powered on by pressing and holding the POWER KEY for 5 seconds. Set the timer to 20 seconds by pressing the MENU KEY. Direct the light beam 1110 into the oral cavity 1101 to an illumination region 1102 under examination with a distance between 2-10 inches. Press ON/OFF KEY to start light. Press ON/OFF KEY anytime during the cycle to stop the light. Each region takes less than 20 seconds to complete the exam. Optical medical diagnostic system suits best to regions difficult to illuminate and requires better light intensity for higher contrast imaging.

Next use violet light assembly 1010 to inspect fluorescence image. To view the illuminated and excitation image, clip-on the loupe filter assembly 1002 to the left and right loupe lens mounts of the magnification loupes 1003. Project the light beam 1110 onto the target tissue 1102. For example, for oral cavity, project the light into oral tissue to inspect. Healthy tissue fluoresces green while suspicious tissue appears dark due to loss of fluorescence. This helps easier and more accurate identification of disease tissue even at its early stage and definition of appropriate margins for surgical procedures.

Figures 12A, 12B:
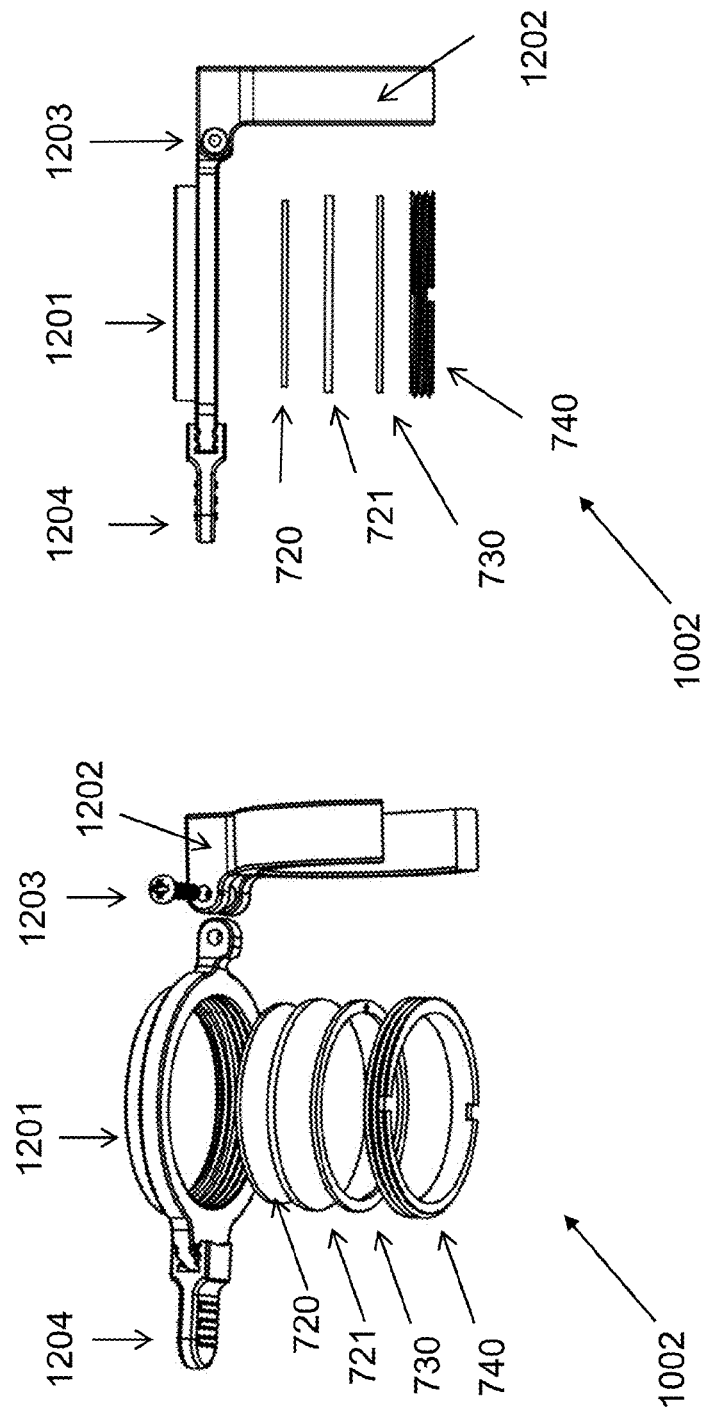
FIG. 12A is an exploded isometric view of one embodiment of a fluorescence loupe filter assembly.
FIG. 12B is an exploded side view of one embodiment of a fluorescence loupe filter assembly.

FIG. 12 shows the exploded view of the fluorescence loupe filter assembly 1002 including a loupe filter holder 1201, detachable filter adjustment tool 1204, semi-circular loupe mounting clip 1202 that is connected with the loupe filter holder 1201 through a mounting screw 1203 which functions as the axis of rotation of the filter holder 1201 from the fixed loupe mounting clip 1202. The loupe filter holder 1201 holds at least one fluorescence filter 720, and preferably a second filter 721 for improved contrast, shock absorbing rubber ring 730, and retaining ring 740 which holds the filters inside the loupe filter holder 1201 using exterior mounting threads tightened onto the mating thread on the internal surface of the filter holder 1201. The loupe filter assembly 1002 mounts on the magnification loupes 1003 through the semi-circular mounting clip 1203.

FIG. 13A illustrates one configuration of the loupe filter assembly 1002 coupled to the magnification loupes 1003 where the loupe filter assembly 1002 is in the viewing field. FIG. 13B illustrates a second configuration of the loupe filter assembly 1002 coupled to the magnification loupes 1003 where the loupe filter assembly 1002 is out of the viewing field. The configurations may be changed through a simple flip on and flip off mechanism using the filter adjustment tools 1204, which can be easily detached from the loupe filter assembly 1002 for disinfection, such as autoclave.

Figure 14:
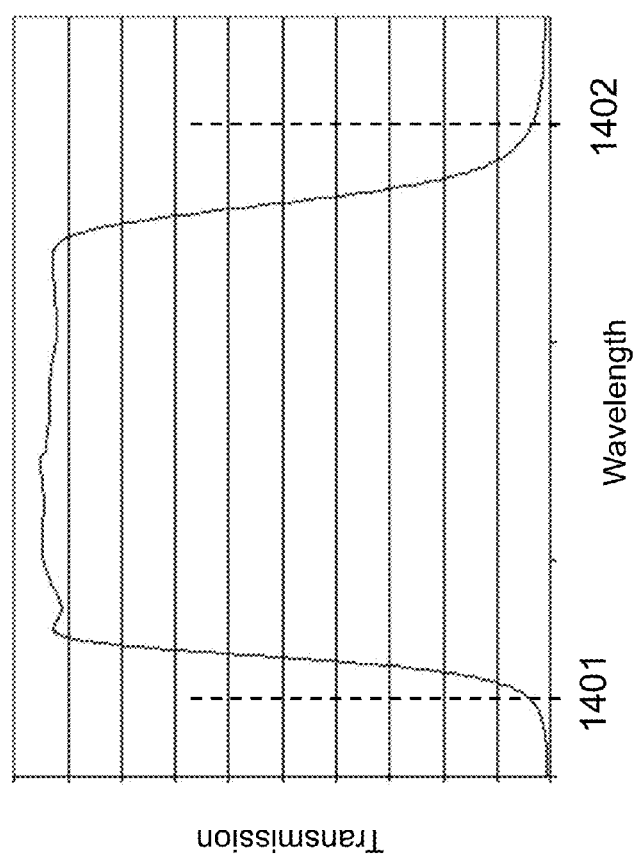
FIG. 14 is a graph illustrating the fluorescence optical filter transmission spectrum of one embodiment of a fluorescence filter.

FIG. 14 illustrates the fluorescence band pass filter transmission profile used in the current invention. The filter allows high contrast transmission of red-shifted fluorescence light in the wavelength with a starting wavelength of 1401 and stop wavelength of 1402. The preferred starting wavelength for 1401 is 480 nm-510 nm and the preferred stop wavelength for wavelength 1402 is 530-580 nm. The fluorescence filter rejects wavelength of the excitation light, for example in the wavelength of 380-430 nm, for enhanced contrast of the fluorescence image. For better contrast, multiple filter cascades, first fluorescence filter 720 and second fluorescence filter 721 as is illustrated in filter assembly 610 and loupe filter assembly 1002, further enhances contrast of fluorescence wavelength and excitation wavelength. The first fluorescence filter 720 and the second fluorescence filter can be the same optical filter with the same optical transmission characteristics or one band pass filter as illustrated in FIG. 14 and a high pass filter with a starting wavelength close to the starting wavelength 1401 of the band pass filter.

The combination of narrow band high power LED excitation source and cascaded band pass high contrast fluorescence filters in addition to well controlled collimated LED illumination beam allows the current device significantly exceed the performance of prior arts.

Figures 15A, 15B:
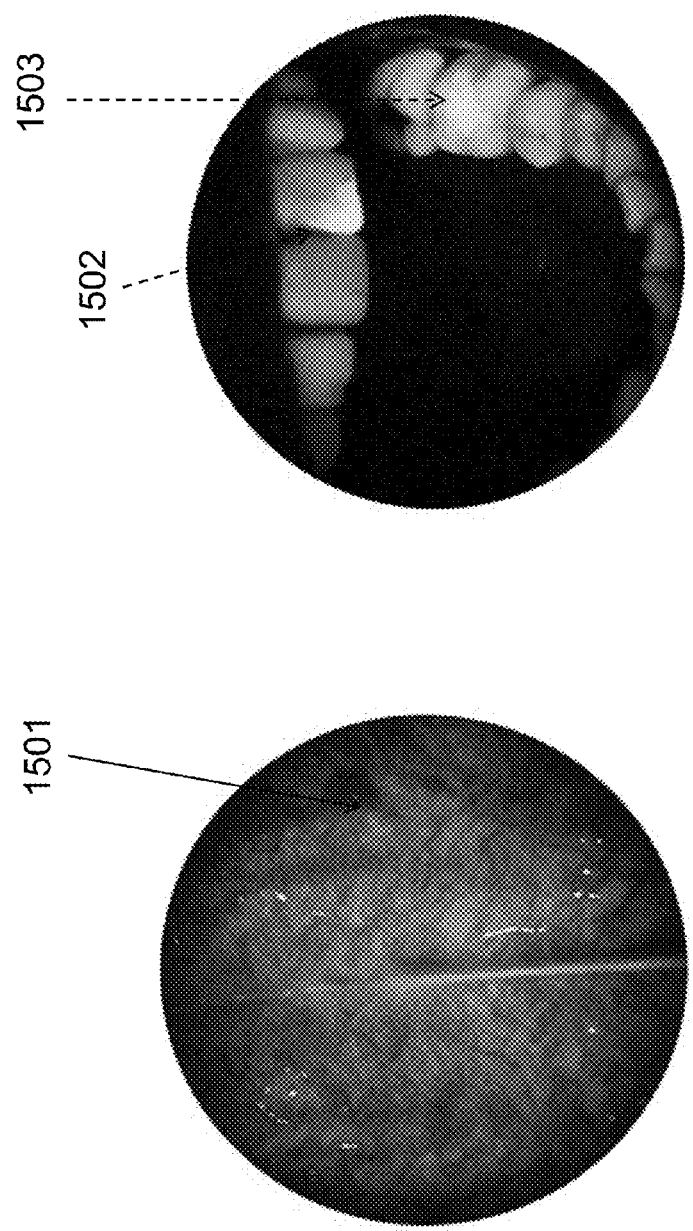
FIG. 15A illustrates a fluorescence image of soft tissues using the optical medical diagnostic system.
FIG. 15B shows the fluorescence image of hard tissues using the optical medical diagnostic system.

FIG. 15 shows the fluorescence images of soft (FIG. 15A) and hard tissue (FIG. 15B) under the current optical medical diagnostic system. The natural color is not reflected here due to the gray scale image.

The contrast of healthy and unhealthy 1501 soft tissue is visible from the image FIG. 15A. Since the current invention has much smaller light assembly and farther reach light beam down to the back of the throat, soft tissue diseases such as dysplasia and early cancerous cells can be identified through the contrast fluorescence imaging.

In hard tissue or teeth, natural teeth will generate fluorescence and composite filling or resins will not. FIG. 15B shows the clear identification of composite 1502 and 1503 in the teeth structure. The benefit of direct distinction of composite from teeth has further applications beyond general tooth exam but restorations from old composite. For example, cavities develop under old composite. To remove the old composite, the current system can be used to identify and define margins or boundaries to clear out the old composite for better restoration of the teeth.

The proposed high efficiency LED optical medical diagnostic system enables versatile and efficient illumination and viewing of fluorescence imaging. The device is particularly useful for portable handheld dental optical medical diagnostic system. It will be apparent to those skilled in the art that various modifications and variations can be made to the present invention without departing from the spirit and scope of the invention. Thus it is intended that the present invention covers the modifications and variations of this invention provided they come within the scope of the appended claims and their equivalents.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

Any advantages and benefits described may not apply to all embodiments of the invention. When the word "means" is recited in a claim element, Applicant intends for the claim element to fall under 35 USC 112, paragraph 6. Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word means are not intended to fall under 35 USC 112, paragraph 6.

The foregoing description of the embodiments of the invention has been presented for the purposes of illustration and description. It is not intended to be exhaustive or to limit the invention to the precise form disclosed. Many combinations, modifications and variations are possible in light of the above teaching. For instance, in certain embodiments, each of the above described components and features may be individually or sequentially combined with other components or features and still be within the scope of the present invention. Undescribed embodiments which have interchanged components are still within the scope of the present invention. It is intended that the scope of the invention be limited not by this detailed description, but rather by the claims.

What is claimed is:

1. An optical medical diagnostic system comprising:
   a light portion comprising:
      a light assembly comprising:
         an LED light source configured to emit violet light between 380 and 430 nm,
         a mounting structure coupled to the LED light source, the mounting assembly having a reflective surface positioned adjacent to the LED light source,
         a Fresnel collimating lens positioned adjacent to the reflective surface and coupled to the mounting structure,
         a transparent cover positioned adjacent to the Fresnel collimating lens and coupled to the Fresnel lens,
      a longitudinal housing,
      wherein the light assembly is positioned on a distal end of the longitudinal housing at a predetermined angle between 5 and 90 degrees,
      a first body connection mechanism coupled to a proximal end portion of the longitudinal housing, and
      a plurality of contact pins in electrical communication with the LED light source and coupled to the proximal end portion of the longitudinal housing,
   a filter assembly comprising:
      a first fluorescence filter,
      a second fluorescence filter,
      a filter holder having cavity sized to receive the first and second fluorescence filter,
      a filter retaining ring adapted to couple to the filter holder,
      a first light hood having exterior mounting threads adapted to couple to the filter holder,
      a semi-circular clip portion rotatably coupled to the filter holder such that the filter holder can rotate with respect to the semi-circular clip portion,
   a controller portion comprising:
      a controller housing,
      control circuitry positioned within the controller housing for sending and receiving control signals to the light source,
      a user interface coupled to the control circuitry and coupled to an external surface of the controller housing,
      a display coupled to the control circuitry and coupled to an external surface of the controller housing,
      a second body connector mechanism positioned on the distal end portion of the controller housing configured to couple with the first body connector mechanism of the light portion such that when the light portion is coupled to the controller portion, the light portion rotates with respect to the controller portion,
   a power portion comprising:
      a rechargeable battery,
      a power housing formed and sized to receive the rechargeable battery.

2. The system of claim 1, wherein the longitudinal housing is formed from a high heat conducting material.

3. The system of claim 1, further comprising a directional collimating hyper-hemispherical lens positioned between the LED light source and the Fresnel collimating lens.

4. The system of claim 1, wherein the head portion is detachable and removable from the control portion.

5. The system of claim 1, wherein the reflective surface is a parabolic reflective surface.

6. The system of claim 1, further comprising a diode heat sink thermally coupled to the LED light source.

7. The system of claim 1, wherein the first body connection mechanism is a O-ring positioned within a groove.

8. The system of claim 1, further comprising a second light assembly having a LED light source configured to emit white light.

9. The system of claim 1, further comprising a third light assembly having a LED light source configured to emit green light between 500 and 580 nm.

10. The system of claim 1, further comprising a fourth light assembly having a LED light source configured to emit blue light between 430 and 490 nm.

11. The system of claim 1, further comprising a convex circumferential ring defined on the exterior surface of the longitudinal housing and a concave slot defined within an interior surface of the semi-circular clip sized to mate with the convex circumferential ring.

12. The system of claim 1, further comprising a second light hood adapted to couple to the first light hood.

13. The system of claim 1, wherein the second body connector mechanism is a ring slot defined within an interior surface of the controller housing.

14. The system of claim 1, wherein the power portion further comprises a controller interface portion for communicating with the controller portion.

15. The system of claim 1, wherein the power portion further comprises a power interface for receiving current from a charging device.

16. The system of claim 1, wherein the power portion further comprises a control board for controlling the battery charging.

17. An optical medical diagnostic system comprising:
a light portion comprising:
   a light assembly comprising:
   an LED light source configured to emit violet light between 380 and 430 nm,
   a mounting structure coupled to the LED light source, the mounting assembly having a reflective surface positioned adjacent to the LED light source,
   a Fresnel collimating lens positioned adjacent to the reflective surface and coupled to the mounting structure,
   a transparent cover positioned adjacent to the Fresnel collimating lens and coupled to the Fresnel lens,
a longitudinal housing,
wherein the light assembly is positioned on a distal end of the longitudinal housing at a predetermined angle between 5 and 90 degrees,
a first body connection mechanism coupled to a proximal end portion of the longitudinal housing, and
a plurality of contact pins in electrical communication with the LED light source and coupled to the proximal end portion of the longitudinal housing,
a controller portion comprising:
a controller housing,
control circuitry positioned within the controller housing for sending and receiving control signals to the light source,
a user interface coupled to the control circuitry and coupled to an external surface of the controller housing,
a display coupled to the control circuitry and coupled to an external surface of the controller housing,
a second body connector mechanism positioned on the distal end portion of the controller housing configured to couple with the first body connector mechanism of the light portion such that when the light portion is coupled to the controller portion, the light portion rotates with respect to the controller portion,
a power portion comprising:
a rechargeable battery,
a power housing formed and sized to receive the rechargeable battery;
a loupe assembly comprising
   a first fluorescence filter,
   a second fluorescence filter,
   a filter holder adapted to hold the first and second fluorescence filters,
   an eye glass assembly adapted to be worn by a human,
      an adapter ring sized to couple with the eye glass assembly,
   a rotating mechanism adapted to rotate the filter holder with respect to the eye glass assembly.

* * * * *